United States Patent
Yaginuma

Patent Number: 5,303,277
Date of Patent: Apr. 12, 1994

[54] PROCESS FOR FABRICATING FUEL ROD AND END PLUG THEREFOR

[75] Inventor: Yoshitaka Yaginuma, Tohkai, Japan

[73] Assignee: Mitsubishi Nuclear Fuel Co., Tokyo, Japan

[21] Appl. No.: 219

[22] Filed: Jan. 4, 1993

[30] Foreign Application Priority Data

Jan. 7, 1992 [JP] Japan ............................ 4-1006

[51] Int. Cl.$^5$ .................................................. G21C 3/10
[52] U.S. Cl. ..................................... 376/451; 376/261
[58] Field of Search ...................... 376/451, 261, 260

[56] References Cited

U.S. PATENT DOCUMENTS

| | | | |
|---|---|---|---|
| 4,003,788 | 1/1977 | Boyko et al. | 376/41 |
| 4,865,804 | 9/1989 | McGeary et al. | 376/451 |
| 5,158,740 | 10/1992 | Boatwright | 376/451 |

Primary Examiner—Donald P. Walsh
Assistant Examiner—Frederick H. Voss
Attorney, Agent, or Firm—Oblon, Spivak, McClelland, Maier & Neustadt

[57] ABSTRACT

A process is presented for fabricating a fuel rod including an elongated fuel tube, a lower end plug for sealing one of the openings, and an upper end plug for sealing an opposite opening. The steps include sealing an opening of the aperture by melting the lead portion of the upper end plug in such way that welding is carried out along the lead portion and a welded portion formed by the welding is disposed below the lower portion of the chamfer. The elongated fuel tube has openings at opposite end thereof, and a plurality of fuel pellets inserted therein. The upper end plug has an end face and an outer peripheral surface, a chamfer formed at an intersection between the end face and the outer peripheral surface, an aperture formed in the center of the upper end plug, a groove formed around the aperture, and a lead portion formed between the aperture and the groove.

4 Claims, 6 Drawing Sheets

B

E F

PROCESS FOR FABRICATING FUEL ROD AND END PLUG THEREFOR

BACKGROUND OF THE INVENTION

The present invention relates to a process for fabricating a fuel rod in which opposite ends of a fuel tube containing a plurality of fuel pellets are sealed with end plugs, and especially to an upper end plug used for said process.

In a conventional method for fabricating a fuel rod, a plurality of fuel pellets are inserted into an elongated fuel tube; a lower end plug is pressed into the lower opening of the fuel tube; a coiled-spring is inserted into the upper opening of the fuel tube; then an upper end plug having an aperture is pressed into the upper opening of the fuel tube. Then, the peripheral surfaces of the end plugs are welded to the fuel tube respectively; helium gas is injected into the fuel tube through the aperture; and the aperture is sealed by welding.

For sealing the aperture of the upper end plug in a conventional manner, an arc welding using a tungsten electrode is applied. However, after an arc is generated between the tungsten electrode and the periphery of the aperture, it is difficult to control the directionality of the arc in a limited area on the end face of the upper end plug, causing the arc to move freely on the end face of the upper end plug. As a result, in some cases, the arc causes melting of a shoulder portion of the upper end plug, because the arc often moves radially outwardly away from the center of the aperture, causing an improper melting of the shoulder portion. Therefore, in order to solve the problem such as above, the applicant suggested a method for welding the center of the aperture stably. In the method, an upper end plug is used having a protrusion formed around the periphery of the aperture of the upper end plug. The protrusion is employed as a lead portion for leading an arc generated in a welding (refer to Laid-open number 62-75377). On the other hand, in a conventional manner, the condition of the welding portion is inspected by transmitting X-ray through the welded portion, but it has been desired to change the X-ray inspection to an ultrasonic inspection. However, a chamfer is formed at the intersection between the end face and the outer peripheral surface of the upper end plug. The edge between the chamfer and the outer peripheral surface of the upper end plug is positioned in the inspection area of the ultrasonic beam. This disturbs the ultrasonic beam irradiated to the inspection area, and the stable inspection cannot be achieved. Therefore, it is difficult to irradiate stably the inspected area with ultrasonic beam. Although it is possible not to form the chamfer, the fabricating of the fuel rod and an assembling process for a fuel assembly may be difficult.

SUMMARY OF THE INVENTION

It is therefore an object of the present invention to present a process for fabricating a fuel rod as to keep the satisfactory condition of the welded portion, and to inspect the condition of the welded portion smoothly and steadily with using supersonic beam.

Moreover it is an object of the present invention to present an end plug used in the abovementioned process.

According to the first aspect of the present invention, there is provided a process for fabricating a fuel rod including an elongated fuel tube having openings at opposite ends thereof, a plurality of fuel pellets inserted in the fuel tube, a lower end plug for sealing one of the openings, and an upper end plug for sealing an opposite opening, said upper end plug comprising, an end face and an outer peripheral surface, a chamfer formed at an intersection between the end face and the outer peripheral surface, an aperture formed in the center of the upper end plug, a groove formed around the aperture, and a lead portion formed between the aperture and the groove, said process comprising the steps of;

sealing an opening of the aperture by melting the lead portion of the upper end plug in such way that welding is carried out along the lead portion, and a welded portion formed by the welding is disposed inwardly of an edge formed between the chamfer and the outer peripheral surface of the upper end plug.

According to the second aspect of the present invention, there is provided a process for fabricating a fuel rod, the bottom of a surface of said welded portion has a longitudinal distance from said end face of the upper end plug larger than the distance to an edge formed at an intersection between the chamfer and the outer peripheral surface of the upper end plug.

According to the third aspect of the present invention, there is provided an end plug for sealing an opening of an fuel tube in which a plurality of fuel pellets are inserted, said end plug comprising, an aperture formed in substantially the center thereof, and a ring-shaped groove formed around the aperture.

According to the third aspect of the present invention, there is provided an end plug, said groove has a V-shaped cross section.

In the process of fabricating a fuel rod and an end plug therefor of the present invention, an upper plug is used into the center of which the aperture is formed which is surrounded by a ring-shaped groove. In the upper plug, a protrusion between the aperture and the ring-shaped groove is used as a lead portion for an arc. When the aperture is sealed by melting of the protrusion, to produce a welded portion disposed below the lower portion of the chamfer formed in the shoulder portion of the upper end plug, the edge which is formed by the outer peripheral surface of the upper end plug and the chamfer, does not disturb with irradiation of the ultrasonic beam to the inspected area.

DESCRIPTION OF THE PREFERRED EMBODIMENT

The preferred embodiment of the present invention will be explained with reference to FIGS. 1 through 7.

Figure 1:
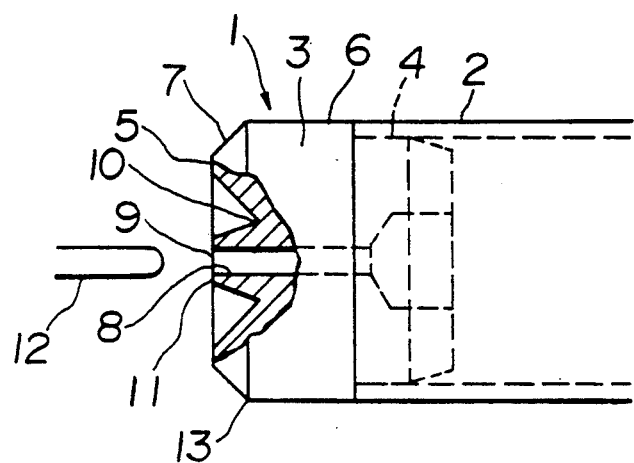
FIG. 1 is a partial cross sectional side view, showing the fuel tube sealed with the upper end plug.
Figure 2:
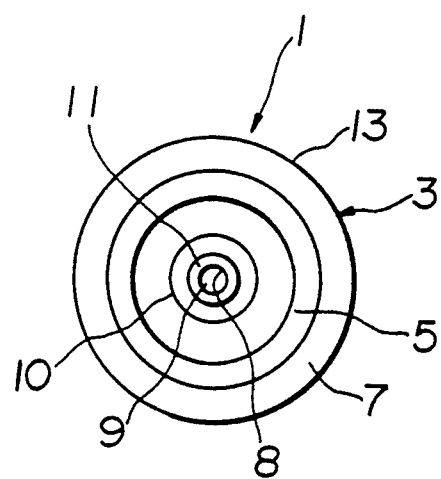
FIG. 2 is a top plan view of the upper end plug shown in FIG. 1.

FIGS. 1 and 2 show an upper end plug 1 and a fuel tube 2 of an embodiment of the present invention. The upper end plug 1 comprises a plug body 3. A slender portion is formed on an end of the plug body 3. The diameter of the slender portion 4 is smaller than the diameter of the plug body 3. The slender portion 4 is inserted into an opening of the fuel tube 2. A chamfer 7 is formed at the intersection between the upper end face 5 and the outer peripheral surface 6 of the plug body 3. An aperture 8 is formed in the center of the plug body 3. Moreover, a ring-shaped groove 10 is formed around the opening 9 of the aperture 8 so as to be concentric with the aperture 8. The cross section of the ring-shaped groove 10 is in shape of a "V". For this structure, a protrusion 11 is formed between the groove 10 and the aperture 8, so that the protrusion 11 is employed for a lead portion for leading an arc generated in a welding. After the upper end plug 1 is pressed into the opening of the fuel tube 2, the upper end plug 1 constructed as above is welded to the fuel tube 2.

Figure 3:
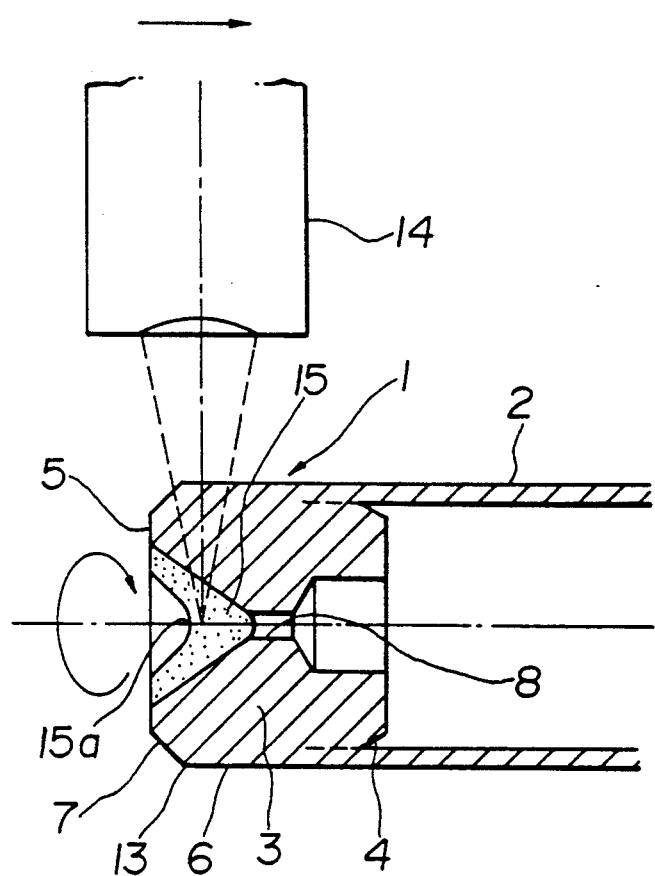
FIG. 3 is a longitudinal cross sectional view showing the state of the ultrasonic inspection of the welded portion of the upper end plug.

The process for fabricating a fuel rod will be explained in the following with reference to FIGS. 1 through 3.

A plurality of fuel pellets are inserted into the elongated fuel tube 2. The lower end plug is pressed into the lower opening of the fuel tube 2. A coiled-spring is inserted into the upper opening of the fuel tube 2. Then the upper end plug 1 having the aperture 8 is pressed into the upper opening of the fuel tube 2. The edge portion of side surfaces of the upper end plug 1 is welded to the side surfaces of the fuel tube 2. Pressurized helium gas is injected into the fuel tube 2 through the aperture 8. The aperture 8 is sealed by arc welding.

In the sealing process, a protrusion 11 formed between the aperture 8 and the ring-shaped groove 10 having a V-shaped cross section is used as a lead portion for leading an arc generated in a welding. The sealing process is carried out in such a way that a tungsten electrode 12 is brought slowly close to the protrusion 11 while a constant voltage is being applied to the tungsten electrode 12. The tungsten electrode 12 used in this process is for constant current welding. When the tungsten electrode 12 is brought sufficiently close to the protrusion 11, the current is generated and begins to flow between them. Then the protrusion 11 of the upper end plug 1 melts by the arc energy. When the current begins to flow, it can be stopped by approaching the tungsten electrode 12 to the protrusion 11. When the protrusion 11 begins to melt, the distance between the top of the protrusion 11 and the end of the tungsten electrode 12 becomes too long. In order to maintain the setting voltage, the position of the tungsten electrode 12 is controlled by the feed back of the instantaneous voltage. When the welding is carried out for a necessary time, the welding process is stopped by cutting off the power supply to the electrode 12. Then the tungsten electrode 12 is put away.

In this way, because the protrusion 11 formed between the aperture 8 and the ring-shaped groove 10 having a V-shaped cross section is used as a lead portion for leading an arc generated in a welding, the welding of the aperture 8 is carried out smoothly without generating a defect such as a melting of a shoulder portion of the upper end plug 1. Moreover, because the position of the bottom portion 15a of the welded portion 15 of the aperture 8 is disposed inwardly of the edge 13 formed between the chamfer 7 and the outer peripheral surface 6 of the upper end plug 1, the edge 13 existing between the outer peripheral surface 6 and the chamfer 7 do not interfere with the ultrasonic beam from ultrasonic tester 14 irradiated to the inspection area. Therefore, because the welded portion 15 is irradiated with the ultrasonic beam stably, the inspection of the welded portion 15 is carried out smoothly, and the flaw detection such as insufficient penetration, and existing pores are discovered easily.

Figure 4:
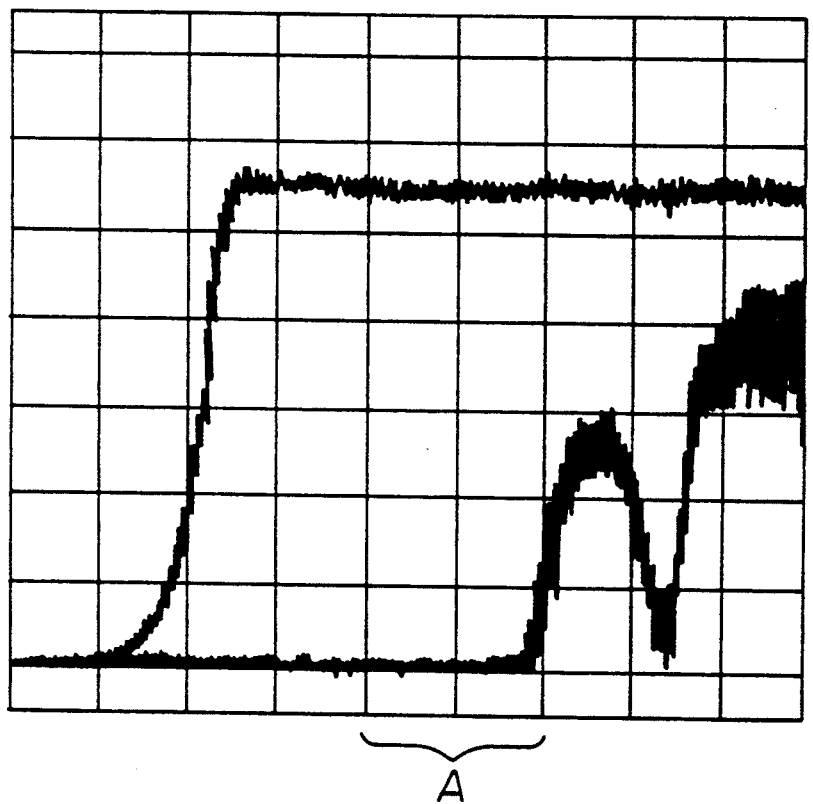
FIG. 4 is a chart showing the ultrasonic inspection result of the condition of welded portion, when welding of the aperture is carried out correctly.
Figure 5:
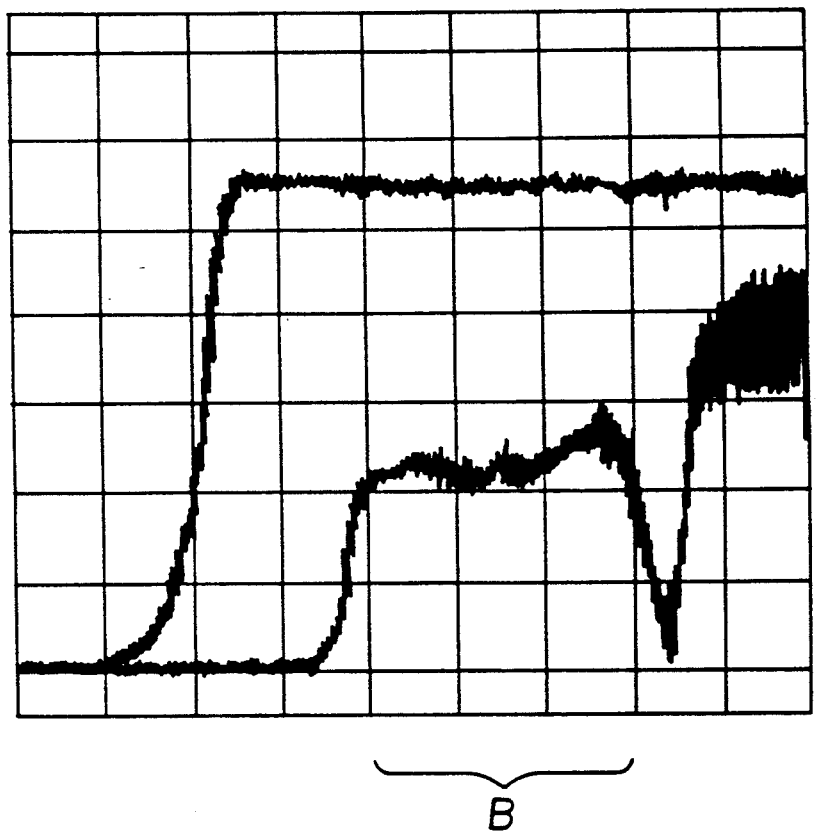
FIG. 5 is a chart showing the ultrasonic inspection result of the aperture of the upper end plug before welding.
Figure 6:
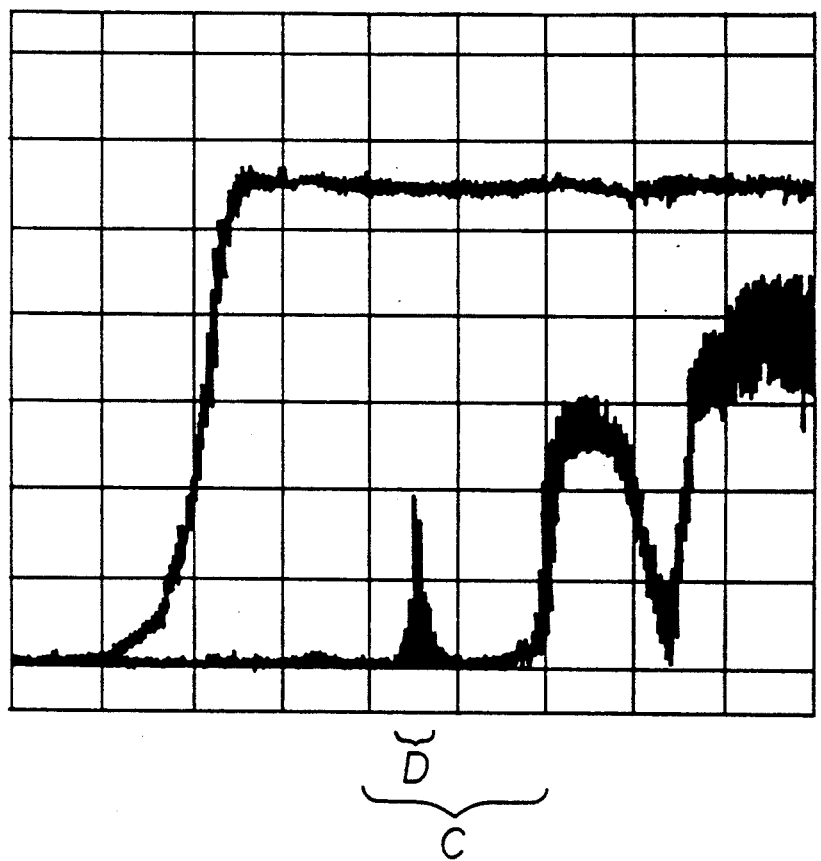
FIG. 6 is a chart showing the ultrasonic inspection result of the welded portion of the upper end plug having porosity defects in the welded portion.
Figure 7:
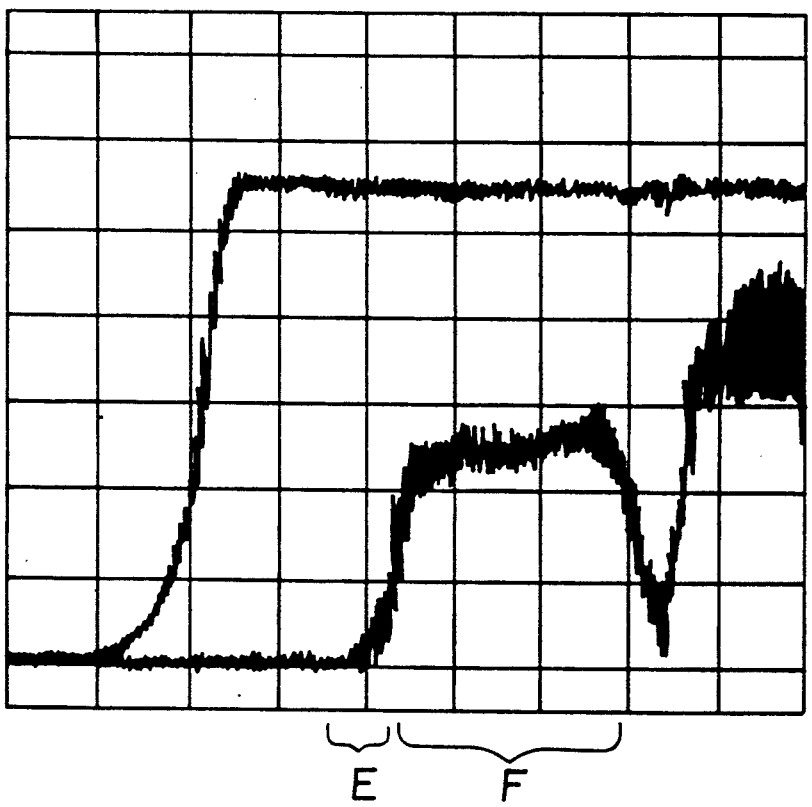
FIG. 7 is a chart showing the ultrasonic inspection result of the welded portion of the upper end plug, when welding of the aperture is insufficient.

FIGS. 4 through 7 show the chart showing the ultrasonic inspection result of the condition of the welded portion 15. FIG. 4 shows the condition of the welded portion 15 when welding of the aperture 8 is carried out correctly (it is judged from the portion indicated with a symbol "A" that welding of the aperture 8 was carried out correctly). FIG. 5 shows the inspection result of the condition of the aperture 8, when the aperture 8 is not welded (it is judged from the portion indicated by "B" that welding is complete). FIG. 6 shows the inspection result of the welded portion indicated by "C". It is judged from the portion indicated by "D" that a porosity defect exists into the welded portion indicated by "C". FIG. 7 shows there is a normal welded portion indicated by "E" and a non-welded portion indicated by "F" formed by the weld penetrating insufficiently. It is understood from the charts of FIGS. 4 through 7 that when carrying out the process for fabricating a fuel rod using an abovementioned end plug according to the present invention, the inspection of the condition of the welded portion 15 is not disturbed with the abovementioned edge 13.

What is claimed:

1. A process for fabricating a fuel rod including an elongated fuel tube having openings at opposite ends thereof, a plurality of fuel pellets inserted in the fuel tube, a lower end plug for sealing one of the openings, and an upper end plug for sealing an opposite opening, said upper end plug comprising an end face, an outer peripheral surface, a chamfer formed at an intersection between the end face and the outer peripheral surface, an aperture formed in the center of the upper end plug, a groove formed around the aperture, and a lead portion formed between the aperture and the groove, said process comprising the steps of;

sealing an opening of the aperture by melting the lead portion of the upper end plug in such way that welding is carried out along the lead portion, and a welded portion formed by the welding is disposed inwardly of an edge formed between the chamfer and the outer peripheral surface of the upper end plug.

2. A process for fabricating a fuel rod in accordance with claim 1, wherein the bottom of a surface of said welded portion has a longitudinal distance from said end face of the upper end plug larger than the distance to an edge formed at an intersection between the chamfer and the outer peripheral surface of the upper end plug.

3. An end plug for sealing an opening of a fuel tube in which a plurality of fuel pellets are inserted, said end plug comprising, an aperture formed in substantially the center thereof, and a ring-shaped groove formed around the aperture.

4. An end plug in accordance with claim 3, wherein said groove has a V-shaped cross section.

* * * * *